US011252343B2

(12) United States Patent
Morales Delgado et al.

(10) Patent No.: US 11,252,343 B2
(45) Date of Patent: Feb. 15, 2022

(54) OPTICAL IMAGING THROUGH DISPLAY

(71) Applicant: Open Water Internet Inc., San Francisco, CA (US)

(72) Inventors: Edgar Emilio Morales Delgado, San Francisco, CA (US); Caitlin Regan, Sausalito, CA (US); Mary Lou Jepsen, Sausalito, CA (US)

(73) Assignee: Open Water Internet Inc., San Francisco, CA (US)

(*) Notice: Subject to any disclaimer, the term of this patent is extended or adjusted under 35 U.S.C. 154(b) by 0 days.

(21) Appl. No.: 17/005,908

(22) Filed: Aug. 28, 2020

(65) Prior Publication Data

US 2020/0396396 A1    Dec. 17, 2020

Related U.S. Application Data

(63) Continuation of application No. 15/942,482, filed on Mar. 31, 2018, now Pat. No. 10,778,912.

(51) Int. Cl.
| | |
|---|---|
| *H04N 5/33* | (2006.01) |
| *G03H 1/04* | (2006.01) |
| *G03H 1/22* | (2006.01) |
| *A61B 8/15* | (2006.01) |
| *A61B 8/00* | (2006.01) |
| *A61B 5/00* | (2006.01) |

(52) U.S. Cl.
CPC .............. *H04N 5/33* (2013.01); *G03H 1/0443* (2013.01); *G03H 1/2294* (2013.01); *G03H 2001/0452* (2013.01); *G03H 2222/16* (2013.01)

(58) Field of Classification Search
CPC ............... G03H 1/0443; G03H 1/2294; G03H 2001/0452; G03H 2222/16; G03H 2001/0083; G03H 2001/0088; G03H 2001/0456; G03H 2210/30; G03H 2210/63; H04N 5/33; A61B 5/0059; A61B 5/00977; A61B 5/68; A61B 8/15; G10K 15/04
USPC .......................................................... 348/40
See application file for complete search history.

(56) References Cited

U.S. PATENT DOCUMENTS

| | | | |
|---|---|---|---|
| 3,573,362 | A | 4/1971 | Burchardt |
| 5,203,339 | A | 4/1993 | Knuttel et al. |
| 5,777,742 | A | 7/1998 | Marron |
| 6,172,760 | B1 | 1/2001 | Son et al. |
| 6,608,774 | B1 | 8/2003 | Rentzepis |

(Continued)

FOREIGN PATENT DOCUMENTS

| | | |
|---|---|---|
| WO | 9110170 A1 | 7/1991 |
| WO | 2017096609 A1 | 6/2017 |

OTHER PUBLICATIONS

Arridge et al. Nonuniqueness in diffusion-based optical tomography, Optics Letters, Jun. 1, 1998, vol. 23, No. 11, pp. 882-884.

(Continued)

*Primary Examiner* — Christopher S Kelley
*Assistant Examiner* — Kathleen M Walsh
(74) *Attorney, Agent, or Firm* — Freestone Intellectual Property Law PLLC; Aaron J. Visbeek

(57) ABSTRACT

An image pixel array captures and infrared image of an interference between an imaging signal and a reference wavefront. A display pixel array generates an infrared holographic imaging signal and the image pixel array receives the infrared imaging signal through the display pixel array.

19 Claims, 15 Drawing Sheets

(56) References Cited

U.S. PATENT DOCUMENTS

| | | |
|---|---|---|
| 6,870,604 B2 | 3/2005 | Kanatake |
| 6,956,650 B2 | 10/2005 | Boas et al. |
| 7,119,906 B2 | 10/2006 | Pepper et al. |
| 7,460,248 B2 | 12/2008 | Kurtz et al. |
| 7,551,809 B2 | 6/2009 | Taira et al. |
| 7,610,082 B2 | 10/2009 | Chance |
| 7,630,126 B2 | 12/2009 | McKinstrie |
| 7,647,091 B2 | 1/2010 | Ntziachristos et al. |
| 7,728,986 B2 | 6/2010 | Lasker et al. |
| 7,764,423 B2 | 7/2010 | McKinstrie et al. |
| 7,804,070 B1 | 9/2010 | Pan et al. |
| 7,821,640 B2 | 10/2010 | Koenig et al. |
| 7,822,468 B2 | 10/2010 | Stamnes et al. |
| 7,826,878 B2 | 11/2010 | Alfano et al. |
| 7,898,649 B2 | 3/2011 | Masumura |
| 7,928,896 B2 | 4/2011 | Jin et al. |
| 7,965,389 B2 | 6/2011 | Silva et al. |
| 7,983,740 B2 | 7/2011 | Culver et al. |
| 8,014,847 B2 | 9/2011 | Shastri et al. |
| 8,120,784 B2 | 2/2012 | Silva et al. |
| 8,170,651 B2 | 5/2012 | Lorenzo et al. |
| 8,239,006 B2 | 8/2012 | Zhu et al. |
| 8,263,947 B2 | 9/2012 | Silva et al. |
| 8,289,502 B2 | 10/2012 | Yoshida |
| 8,326,567 B2 | 12/2012 | Masumura |
| 8,330,642 B2 | 12/2012 | Jin et al. |
| 8,355,131 B2 | 1/2013 | Bakker et al. |
| 8,357,915 B2 | 1/2013 | Guyon et al. |
| 8,374,409 B2 | 2/2013 | Jochemsen et al. |
| 8,385,151 B2 | 2/2013 | Liu |
| 8,416,421 B2 | 4/2013 | Wang et al. |
| 8,450,674 B2 | 5/2013 | Yang et al. |
| 8,451,450 B2 | 5/2013 | Heng |
| 8,520,921 B2 | 8/2013 | Ziegler et al. |
| 8,525,998 B2 | 9/2013 | Yaqoob et al. |
| 8,527,242 B2 | 9/2013 | Granot et al. |
| 8,531,662 B2 | 9/2013 | Mark |
| 8,563,932 B2 | 10/2013 | Fang et al. |
| 8,634,077 B2 | 1/2014 | Hu et al. |
| 8,649,015 B2 | 2/2014 | Ichihara et al. |
| 8,654,343 B2 | 2/2014 | Awatsuji et al. |
| 8,717,574 B2 | 5/2014 | Yang et al. |
| 8,792,102 B2 | 7/2014 | Patil et al. |
| 8,814,795 B2 | 8/2014 | Derode et al. |
| 8,817,255 B2 | 8/2014 | Masumura |
| 8,830,573 B2 | 9/2014 | Cui et al. |
| 8,847,175 B2 | 9/2014 | Laidevant et al. |
| 8,896,730 B2 | 11/2014 | Fossum |
| 8,917,442 B2 | 12/2014 | Baym et al. |
| 8,937,284 B2 | 1/2015 | Fang et al. |
| 8,954,130 B2 | 2/2015 | Masumura |
| 8,976,433 B2 | 3/2015 | Masumura |
| 9,012,869 B2 | 4/2015 | Andersson-Engels et al. |
| 9,036,970 B2 | 5/2015 | Guyon et al. |
| 9,037,216 B2 | 5/2015 | Hielscher et al. |
| 9,057,695 B2 | 6/2015 | Masumura |
| 9,131,851 B2 | 9/2015 | Fukutani et al. |
| 9,134,229 B2 | 9/2015 | Lesage et al. |
| 9,179,842 B2 | 11/2015 | Nakaji et al. |
| 9,201,397 B2 | 12/2015 | Awatsuji et al. |
| 9,207,171 B2 | 12/2015 | Nadakuditi et al. |
| 9,232,896 B2 | 1/2016 | Baym et al. |
| 9,234,841 B2 | 1/2016 | Wang et al. |
| 9,239,415 B2 | 1/2016 | Miao et al. |
| 9,282,932 B2 | 3/2016 | Kudo et al. |
| 9,297,752 B2 | 3/2016 | Shimokawa et al. |
| 9,304,490 B2 | 4/2016 | Masumura |
| 9,313,423 B2 | 4/2016 | Wang et al. |
| 9,335,604 B2 | 5/2016 | Popovich et al. |
| 9,335,605 B2 | 5/2016 | Wang et al. |
| 9,341,569 B2 | 5/2016 | Hooft et al. |
| 9,354,166 B2 | 5/2016 | Judkewitz et al. |
| 9,373,020 B2 | 6/2016 | Kudo et al. |
| 9,407,796 B2 | 8/2016 | Dinten et al. |
| 9,427,213 B2 | 8/2016 | Suzuki et al. |
| 9,440,844 B2 | 9/2016 | Salsman |
| 9,480,425 B2 | 11/2016 | Culver et al. |
| 9,486,142 B2 | 11/2016 | Hielscher et al. |
| 9,488,574 B2 | 11/2016 | Koehler et al. |
| 9,497,722 B2 | 11/2016 | Husain et al. |
| 9,503,692 B2 | 11/2016 | Morita et al. |
| 9,509,956 B2 | 11/2016 | Piestun et al. |
| 9,541,776 B2 | 1/2017 | Lin et al. |
| 9,622,663 B2 | 4/2017 | Fang et al. |
| 9,628,732 B2 | 4/2017 | Velichko |
| 9,678,236 B2 | 6/2017 | Rodney et al. |
| 9,689,797 B2 | 6/2017 | Sun et al. |
| 9,724,489 B2 | 8/2017 | Barbour et al. |
| 9,730,649 B1 | 8/2017 | Jepsen |
| 9,750,413 B2 | 9/2017 | Sandusky et al. |
| 10,001,405 B2 | 6/2018 | Awatsuji et al. |
| 10,016,137 B1 | 7/2018 | Yang et al. |
| 10,203,274 B2 | 2/2019 | Ruan et al. |
| 10,219,700 B1 | 3/2019 | Yang et al. |
| 10,292,589 B2 | 5/2019 | Wang et al. |
| 10,299,682 B1 | 5/2019 | Yang et al. |
| 10,368,752 B1 | 8/2019 | Alford et al. |
| 10,420,469 B2 | 9/2019 | Sobek et al. |
| 2003/0067312 A1 | 4/2003 | Pfaff et al. |
| 2003/0139667 A1 | 7/2003 | Hewko et al. |
| 2005/0030603 A1 | 2/2005 | Takemori et al. |
| 2005/0094256 A1 | 5/2005 | Dane et al. |
| 2005/0270530 A1 | 12/2005 | Wada et al. |
| 2006/0152783 A1 | 7/2006 | Butler et al. |
| 2009/0076389 A1 | 3/2009 | Jin et al. |
| 2009/0115921 A1 | 5/2009 | Fujinoki et al. |
| 2010/0016732 A1 | 1/2010 | Wells et al. |
| 2010/0051785 A1 | 3/2010 | Dai et al. |
| 2010/0103505 A1 | 4/2010 | McKinstrie et al. |
| 2010/0315638 A1 | 12/2010 | Goohs et al. |
| 2011/0071402 A1 | 3/2011 | Masumura |
| 2011/0125014 A1 | 5/2011 | Derode et al. |
| 2011/0205409 A1 | 8/2011 | Fossum |
| 2011/0292402 A1 | 12/2011 | Awatsuji et al. |
| 2011/0317519 A1 | 12/2011 | Liu |
| 2012/0051176 A1 | 3/2012 | Liu |
| 2012/0052947 A1* | 3/2012 | Yun .................. A63F 13/833 463/32 |
| 2012/0070817 A1* | 3/2012 | Wang ................. G01N 21/1717 435/3 |
| 2012/0182591 A1 | 7/2012 | Masumura |
| 2012/0220840 A1 | 8/2012 | Morita et al. |
| 2012/0300608 A1 | 11/2012 | Masumura |
| 2012/0307250 A1 | 12/2012 | Wang et al. |
| 2013/0100333 A1 | 4/2013 | Awatsuji et al. |
| 2013/0116926 A1 | 5/2013 | Rodney et al. |
| 2013/0170785 A1 | 7/2013 | Gao |
| 2013/0276542 A1 | 10/2013 | Herzog et al. |
| 2013/0301093 A1 | 11/2013 | Awatsuji et al. |
| 2013/0342665 A1 | 12/2013 | Wang et al. |
| 2014/0009808 A1 | 1/2014 | Wang et al. |
| 2014/0028804 A1 | 1/2014 | Usuda et al. |
| 2014/0049631 A1 | 2/2014 | Sun et al. |
| 2014/0081096 A1 | 3/2014 | Baym et al. |
| 2014/0114181 A1 | 4/2014 | Wu et al. |
| 2014/0118739 A1 | 5/2014 | Judkewitz et al. |
| 2014/0126567 A1 | 5/2014 | Husain et al. |
| 2014/0267598 A1 | 9/2014 | Drouin et al. |
| 2014/0303473 A1 | 10/2014 | Nanaumi |
| 2014/0347672 A1 | 11/2014 | Pavilion et al. |
| 2015/0015879 A1 | 1/2015 | Papadopoulos et al. |
| 2015/0054973 A1 | 2/2015 | Velichko |
| 2015/0101411 A1 | 4/2015 | Zalev et al. |
| 2015/0182121 A1 | 7/2015 | Barbour et al. |
| 2015/0238092 A1 | 8/2015 | Masumura |
| 2015/0241342 A1 | 8/2015 | Zhou et al. |
| 2015/0285739 A1 | 10/2015 | Nadakuditi et al. |
| 2015/0346027 A1 | 12/2015 | Khare et al. |
| 2015/0351635 A1 | 12/2015 | Cerussi et al. |
| 2016/0061656 A1 | 3/2016 | Awatsuji et al. |
| 2016/0081556 A1 | 3/2016 | Dreher |
| 2016/0085135 A1 | 3/2016 | Park et al. |

(56) References Cited

U.S. PATENT DOCUMENTS

| | | |
|---|---|---|
| 2016/0157723 A1 | 6/2016 | Kanick et al. |
| 2016/0198954 A1 | 7/2016 | Wang et al. |
| 2016/0216503 A1 | 7/2016 | Kim et al. |
| 2016/0262723 A1 | 9/2016 | Zhu |
| 2016/0363527 A1 | 12/2016 | Ruan et al. |
| 2017/0074985 A1 | 3/2017 | Christmas |
| 2017/0086160 A1 | 3/2017 | Smith et al. |
| 2017/0118423 A1 | 4/2017 | Zhou et al. |
| 2017/0156600 A1 | 6/2017 | Ntziachristos et al. |
| 2017/0163946 A1 | 6/2017 | Komanduri et al. |
| 2017/0168565 A1 | 6/2017 | Cohen et al. |
| 2017/0202633 A1 | 7/2017 | Liu |
| 2017/0205767 A1 | 7/2017 | Rosen |
| 2017/0212407 A1 | 7/2017 | Hunt |
| 2017/0230555 A1 | 8/2017 | Tabirian et al. |
| 2017/0231501 A1 | 8/2017 | Culver et al. |
| 2018/0070891 A1 | 3/2018 | Jepsen |
| 2018/0074458 A1 | 3/2018 | Tsang et al. |
| 2018/0335753 A1 | 11/2018 | Jepsen et al. |
| 2019/0008388 A1 | 1/2019 | Ando et al. |
| 2019/0072897 A1 | 3/2019 | Jepsen et al. |
| 2019/0083059 A1 | 3/2019 | Byrnes et al. |
| 2019/0129162 A1 | 5/2019 | Hodelin |
| 2019/0150745 A1* | 5/2019 | Sobek ............... A61B 5/7278 |
| 2019/0258061 A1 | 8/2019 | Solomon |
| 2019/0306437 A1 | 10/2019 | Delgado et al. |
| 2019/0306439 A1 | 10/2019 | Delgado et al. |
| 2019/0336057 A1 | 11/2019 | Alford et al. |

OTHER PUBLICATIONS

Dovhaliuk, Review of digital holography reconstruction methods, Thirteenth International Conference on Correlation Optics, Jan. 2018.

Eggebrecht, Adam T., Mapped distributed brain function and networks with diffuse optical tomography, Nat Photonics, Jun. 2014; 8(6): 458-464.

Freund et al. Memory Effects in Propagation of Ooptical Waves through Disordered Media, Physical Review Letters, Nov. 14, 1988, vol. 61, No. 20, pp. 2328-2331.

Goodman et al. Wavefront-Reconstruction Imaging Through Random Media, Jun. 15, 1966, vol. 8, No. 12, pp. 311-313.

Harrach, Bastian, On uniqueness in diffuse optical tomography, InverseProblems 25 2009, IOP Publishing Ltd.

Hofmann et al. Differential light detector, Rev. Sci. Instrum, Feb. 1979, vol. 50, No. 2, paes 249-252.

Leith, Emmet N., Holographic Imagery through Diffusing Media, Journal of the Optical Society of America, Apr. 1966, vol. 56, No. 4.

Peng et al. Low loss liquid crystals for infrared applications, Liquid Crystal, 2014, vol. 41, No. 11, pp. 1545-1552.

Vellekoop, I. M., Focusing coherent light through opaque strongly scattering media, Optics Letters, Aug. 15, 2007, vol. 32, No. 16.

Yamaguchi, Phase-shifting digital holography, Optics Letters, Aug. 15, 1997, 1268-1270, vol. 22, No. 16.

Yaras, Fahri, State of the Art in Holographic Displays: A Survey, Journal of Display Technology, Oct. 2010, vol. 6, No. 10, 443-454.

European Patent Office, Extended European Search Report, European Application No. 19776668.6-120/3373167, PCT/US2019/022256, dated Nov. 25, 2021, 9 pages.

* cited by examiner

OPTICAL IMAGING THROUGH DISPLAY

CROSS-REFERENCE TO RELATED APPLICATIONS

This application is a continuation of pending U.S. non-provisional patent application Ser. No. 15/942,482 filed Mar. 31, 2018 and entitled "System and Device for Optical Transformation," which is hereby incorporated by reference.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
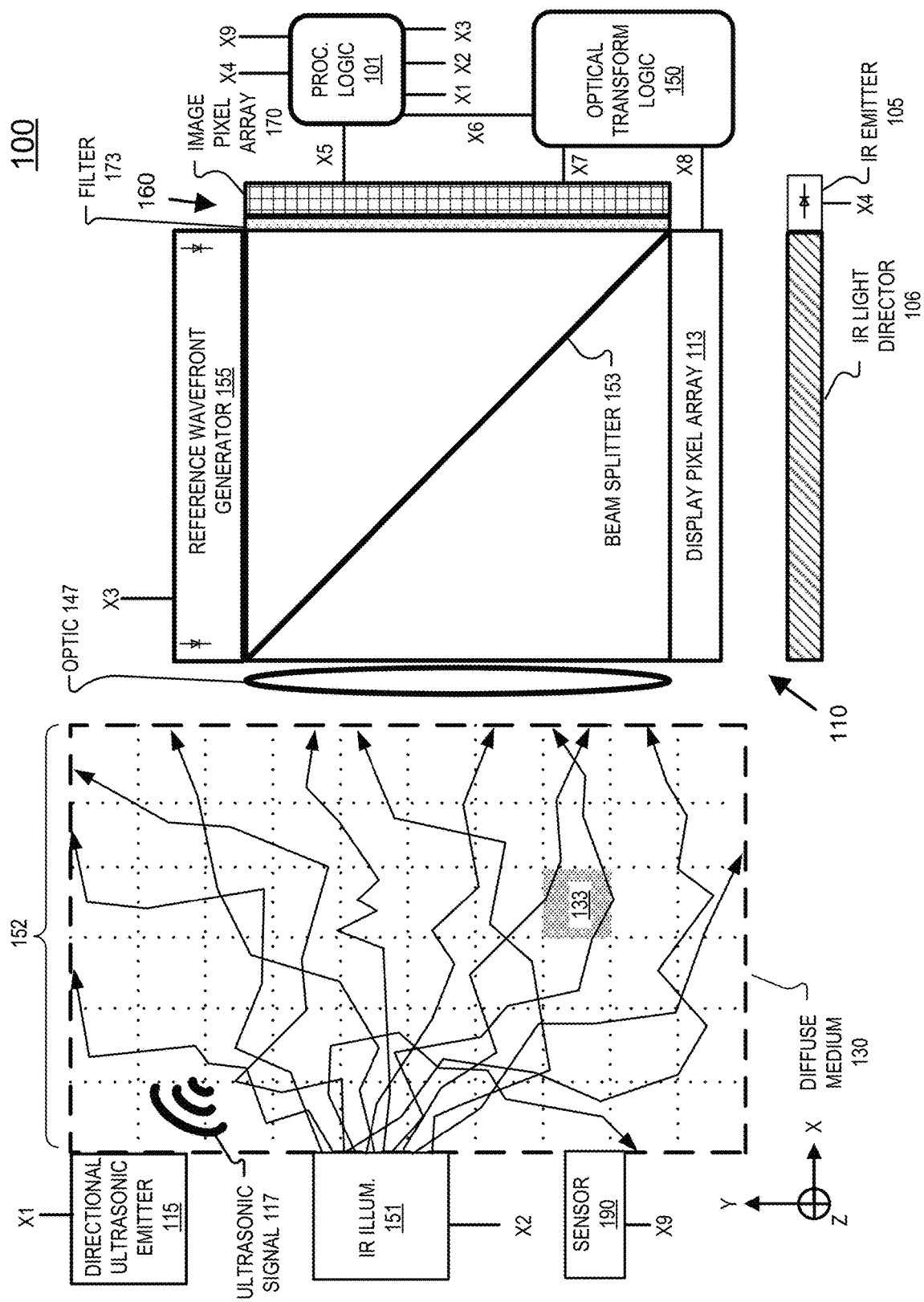
FIGS. 1A-1C illustrate an example imaging system that includes a display pixel array, an image pixel array, and a beam splitter, in accordance with an embodiment of the disclosure.

Embodiments of a system, device, and method for optical imaging of a diffuse medium are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least impeded (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is used at the detector; thus efficacy and power limitations as well as safety limits on input intensity limit TOF imaging resolution and utility.

In contrast to TOF imaging, embodiments of this disclosure utilize a holographic imaging signal to direct infrared light to a voxel of a diffuse medium (e.g. a brain or tissue). A device or system of the disclosure may illuminate a diffuse medium with an infrared light while an ultrasound emitter is focused on a particular voxel. The infrared light encountering the particular voxel may be wavelength-shifted by the ultrasonic signal. The wavelength-shifted infrared imaging signal can be measured by a light detector (e.g. image pixel array). An optical transformation may be performed to generate a holographic pattern to be driven onto a display pixel array. When the display pixel array is illuminated by a light source having the same wavelength as the wavelength shifted infrared imaging signal, (while the holographic pattern is driven onto the display pixel array), a reconstructed version of the received wavelength-shifted infrared imaging signal may be directed back to the voxel to focus on the voxel so that an exit signal generated by the voxel can be measured by a sensor. The exit signal is the infrared light of the holographic beam that is reflected from and/or transmitted through the voxel. By capturing images of the exit signal changes (e.g. oxygen depletion in red blood cells, scattering changes induced by potential differences in an activated neuron, fluorescent contrast agents and other optical changes) at a voxel or group of voxels in the diffuse medium, changes to that voxel or group of voxels can be recorded over time.

In an embodiment of the disclosure, a device or system illuminates a diffuse medium with an infrared light while an ultrasound emitter is focused on a particular voxel. The infrared light encountering the particular voxel may be wavelength-shifted by the ultrasonic signal. The wavelength-shifted infrared imaging signal can be measured by a light detector (e.g. image pixel array). Extraction logic may isolate the wavelength-shifted infrared imaging signal and extract intensity data and then populate a voxel value of a composite image with the intensity data. The composite image may include a three-dimensional image of the diffuse medium.

These embodiments and others will be described in more detail with references to FIGS. 1-10.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise.

Figure 1B:
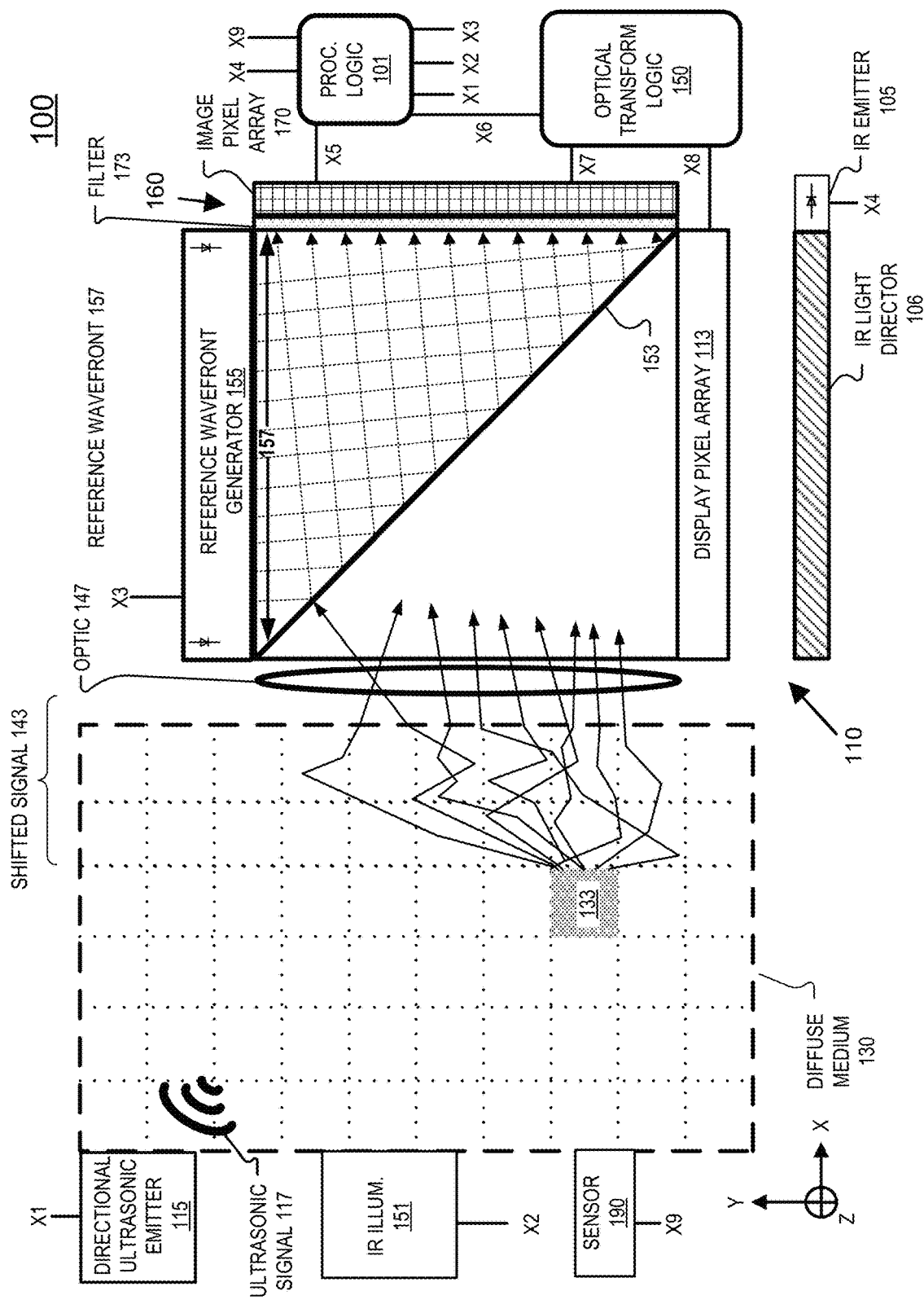
Figure 1C:
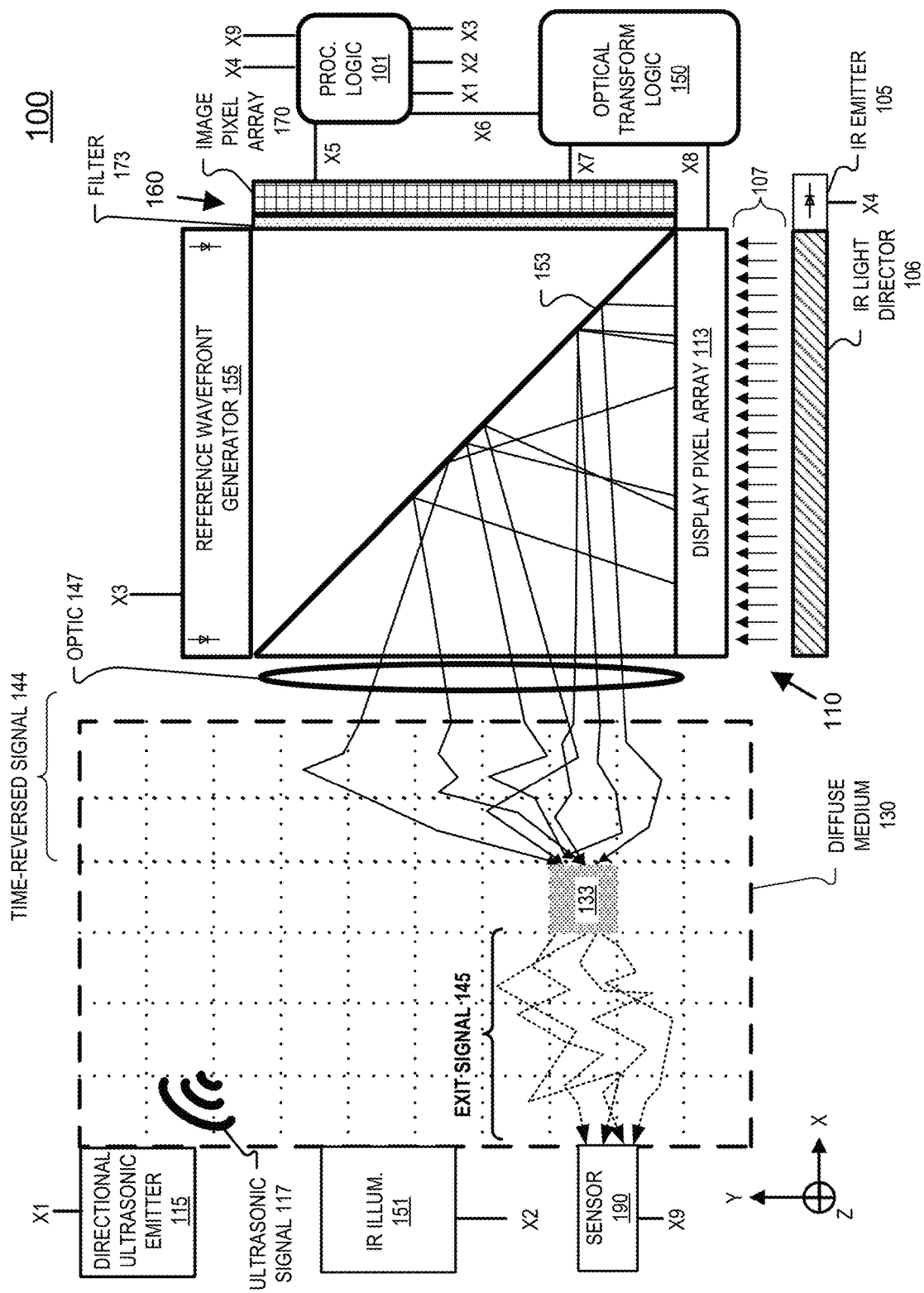

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. The illustrated SLM 110 includes infrared (IR) light director 106 and display pixel array 113 and imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are less than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of general illumination emission 152 that encounters the voxel by wavelength-shifting that portion of the general illumination emission 152.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer.

System 100 receives (at least a portion of) shifted infrared imaging signal 143. An input optic 147 may optionally be included in system 100. Input optic 147 may receive shifted signal 143 and focus the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of the angle threshold is approximately equivalent to a wavelength of the shifted signal 143 (lambda-two) divided by a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image pixel array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may increase the interference between shifted signal 143 and wavefront 157, which may increase the interference signal for capturing by image pixel array 170. Processing logic 101 is coupled to initiate the image capture by image pixel array 170 via output X5, in the illustrated embodiment.

A linear polarizer is included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173, in FIG. 1.

In the illustrated embodiment, an infrared filter 173 is disposed between beam splitter 153 and image pixel array 170. Infrared filter 173 passes the wavelength of infrared light emitted by reference wavefront generator 155 (lamda-two) and rejects other light wavelengths that image pixel array 170 is sensitive to. Infrared filter 173 may be configured to reject ambient light that is other than the lambda-two wavelength.

Image pixel array 170 may be implemented with an a-Si (amorphous Silicon) thin film transistors, in some embodiments or a CMOS (Complimentary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) rather than a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150. for further processing. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is presented below in association with FIGS. 5-7.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern to array 113 via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta) = m\lambda/d \qquad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus the an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
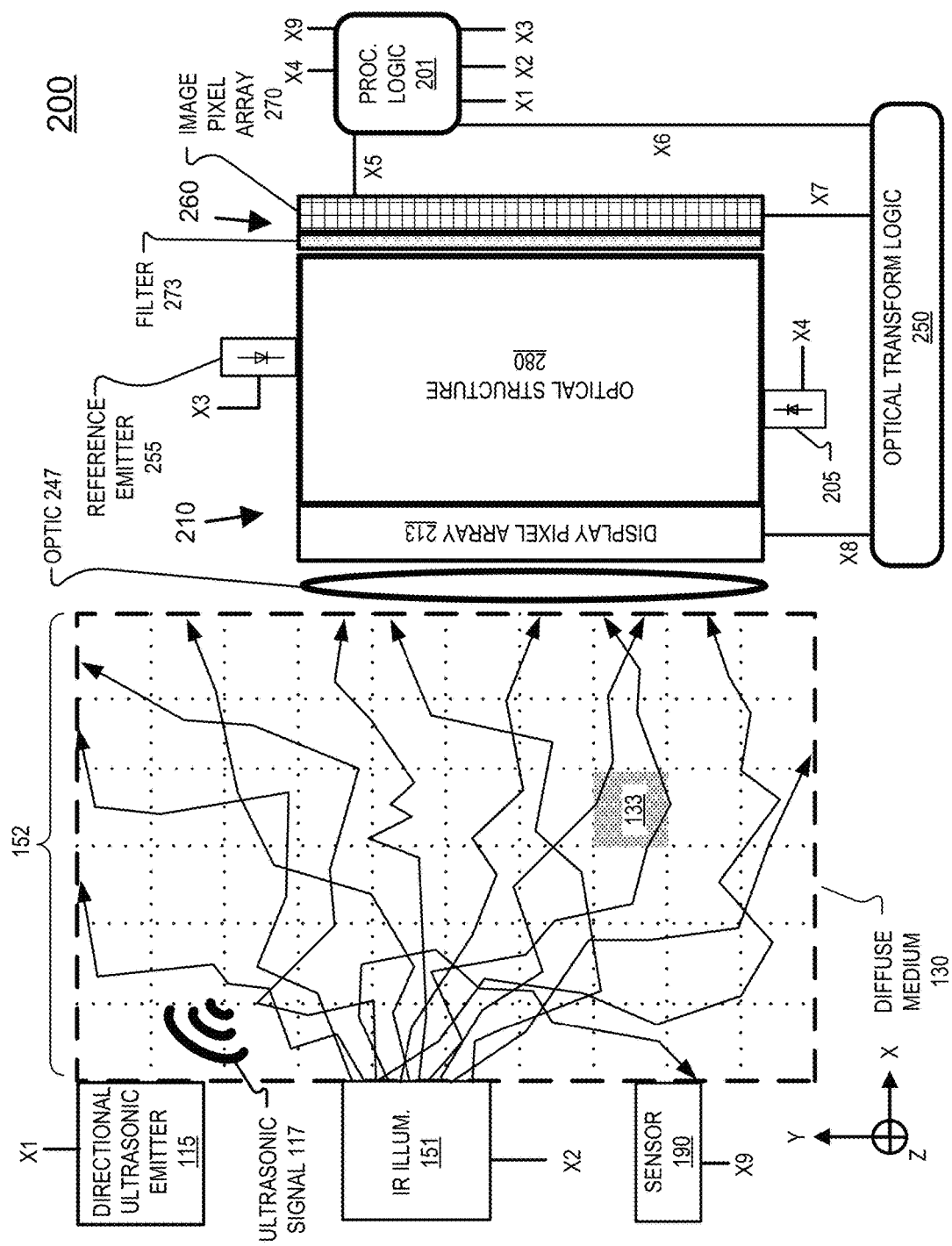
FIGS. 2A-2C illustrate an example imaging system that includes an optical structure disposed between a display pixel array and an image pixel array, in accordance with an embodiment of the disclosure.
Figure 2B:
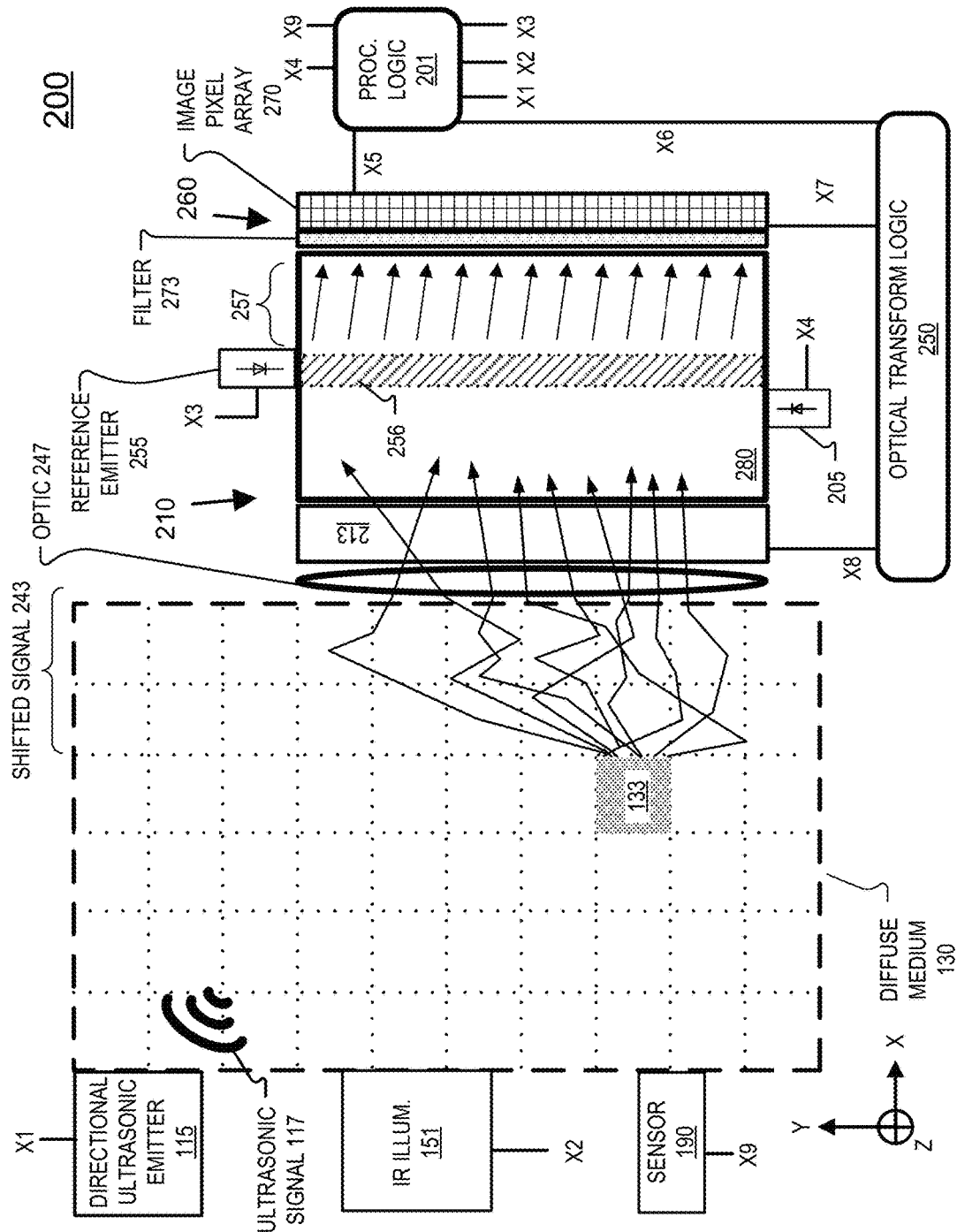
Figure 2C:
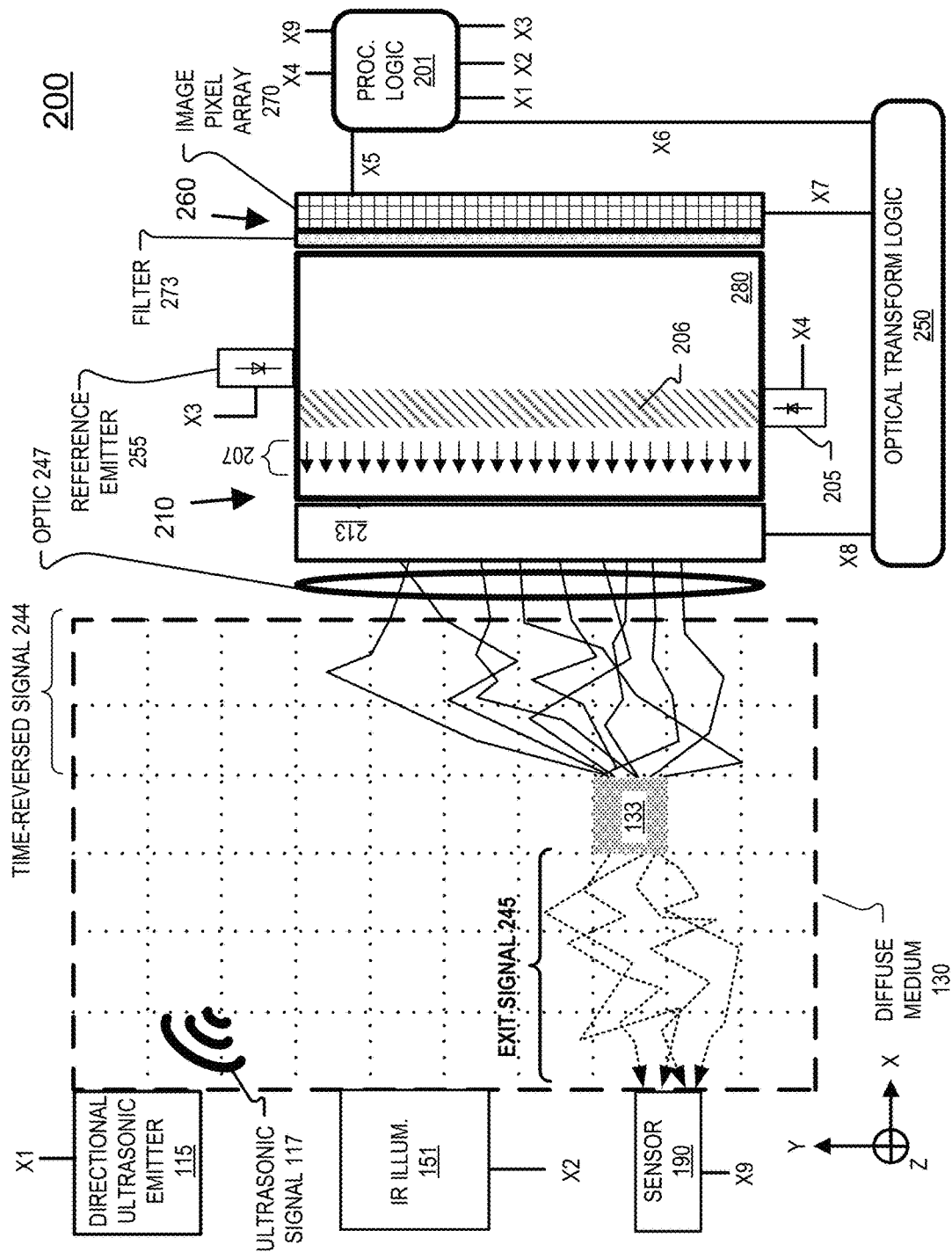

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer is included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Figure 3:
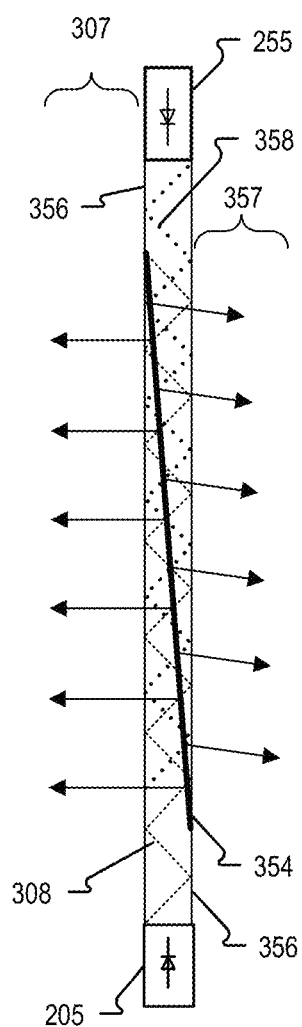
FIG. 3 illustrate an optic that may be included in the optical structure of FIGS. 2A-2C, in accordance with an embodiment of the disclosure.

FIG. 3 illustrates an optic that may be used in the optical structure 280, in accordance with an embodiment of the disclosure. FIG. 3 includes a beam splitter 354 embedded in a light guide 356. Reference emitter 255 is optically coupled to emit the infrared reference light into the light guide 356 along an optical path 358. Infrared emitter 205 is optically coupled to emit an infrared wavefront into the opposite end of light guide 356 along an optical path 308. Light guide 356 may be configured to confine the infrared light propagating in light guide 356 by Total Internal Reflection (TIR). However, the light reflecting off of beam splitter 354 may achieve the critical angle to be outcoupled from the light guide 356 as infrared wavefront 307 (toward display pixel array 213) or as infrared reference wavefront 357 (toward the image pixel array 270). Since beam splitter 354 still passes a portion of incident light, at least a portion of the shifted signal 243 will still reach image pixel array 270 when the configuration of FIG. 3 is used in optical structure 280.

In one embodiment (not illustrated), optical structure 280 includes a slim optic including a graduated gradient grating and the reference emitter is disposed to emit the infrared reference light at an edge of the graduated gradient grating. The graduated gradient grating is configured to increase a percentage of the infrared reference light as a distance from the edge of the graduated gradient grating increases to achieve a substantially uniform infrared reference wavefront 257. In one embodiment, an electronically switchable hologram may be included in optical structure 280 and the electronically switchable hologram may be activated to direct the infrared reference wavefront 257 to image pixel array 270 when the reference emitter 255 is activated. Another electronically switchable hologram may be activated when infrared emitter 205 is activated to directed infrared light 207 to illuminate display pixel array 213.

Returning again to FIG. 2B, shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiment, image pixel array 170 may be angled to increase the signal of interference between the infrared reference wavefront 157 and shifted signal 143.

Figure 4:
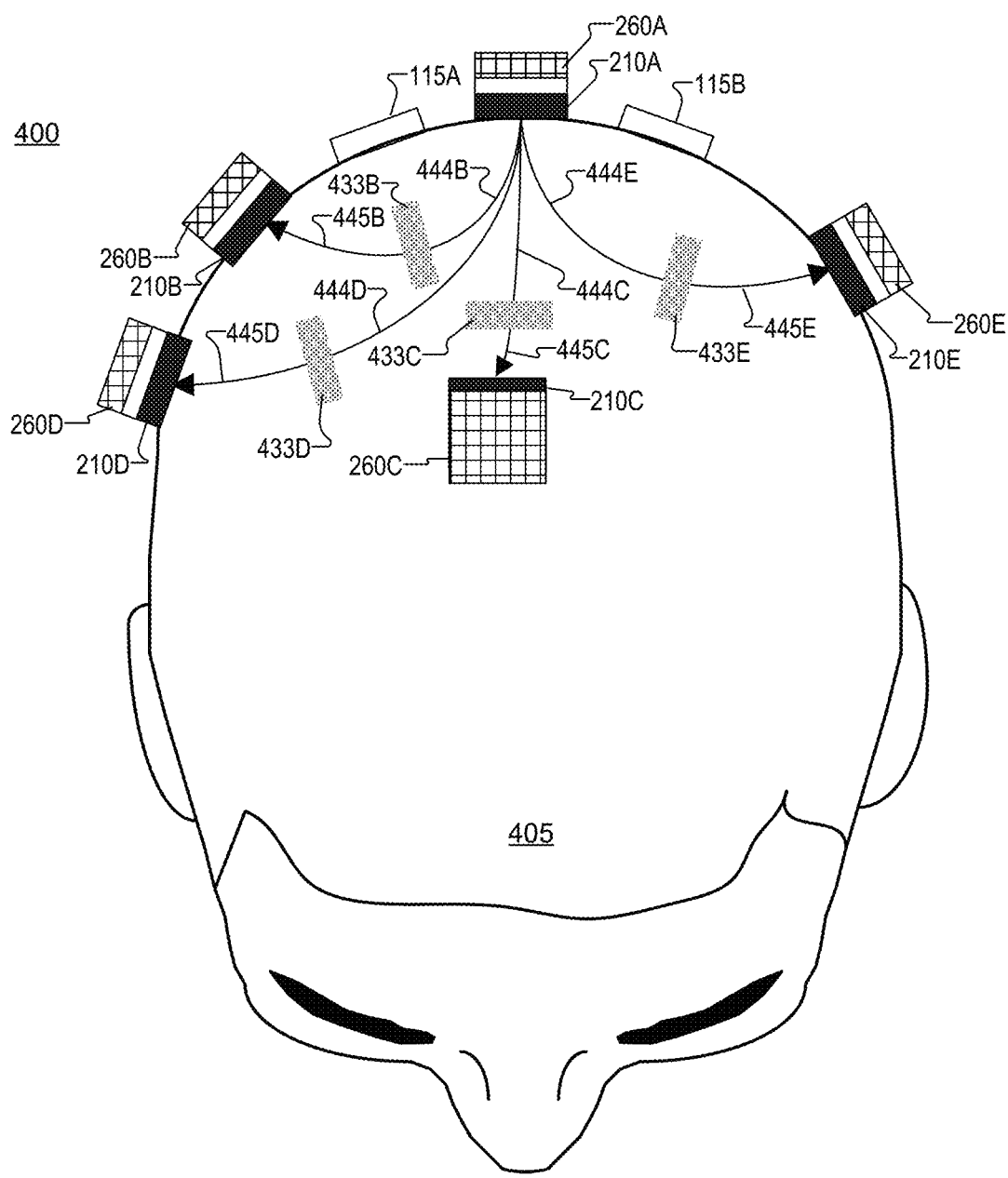
FIG. 4 illustrates an example placement of components of an imaging system in relationship to a human head, in accordance with an embodiment of the disclosure.

FIG. 4 illustrates an example placement of components of an imaging system 400 in relationship to a human head, in accordance with an embodiment of the disclosure. FIG. 4 is a top-down view of a human head 405. Imaging system 400 includes SLMs 210A-210E and imaging modules 260A-260E arranged as in system 200, and directional ultrasonic emitters 115A and 115B. Of course, SLMs 110 and imaging modules 160 coupled also be used instead of SLMs 210 and imaging modules 260 in imaging system 400. FIG. 4 shows that SLM 110A may generate multiple reconstructed infrared signals 444 that are directed to image different voxels 433 of the brain while the exit signals 445 are imaged by different imaging modules 160. The other SLMs 110B-110E may also send reconstructed infrared signals 444 (not illustrated) to each of imaging modules 160A-E. Scientific literature suggests that the penetration depth of infrared light into tissue is around 10 cm so multiple SLMs 110 and imaging modules 160 may be needed to image the entire brain or other tissue. Although not illustrated, sensors 190 may also be placed around a diffuse medium such as human head 405 to measure the exit signals 445. A wearable hat may include system 400 so that system 400 can be worn as a wearable, in some embodiments. Other wearables may also include all or part of system 400.

Figure 5:
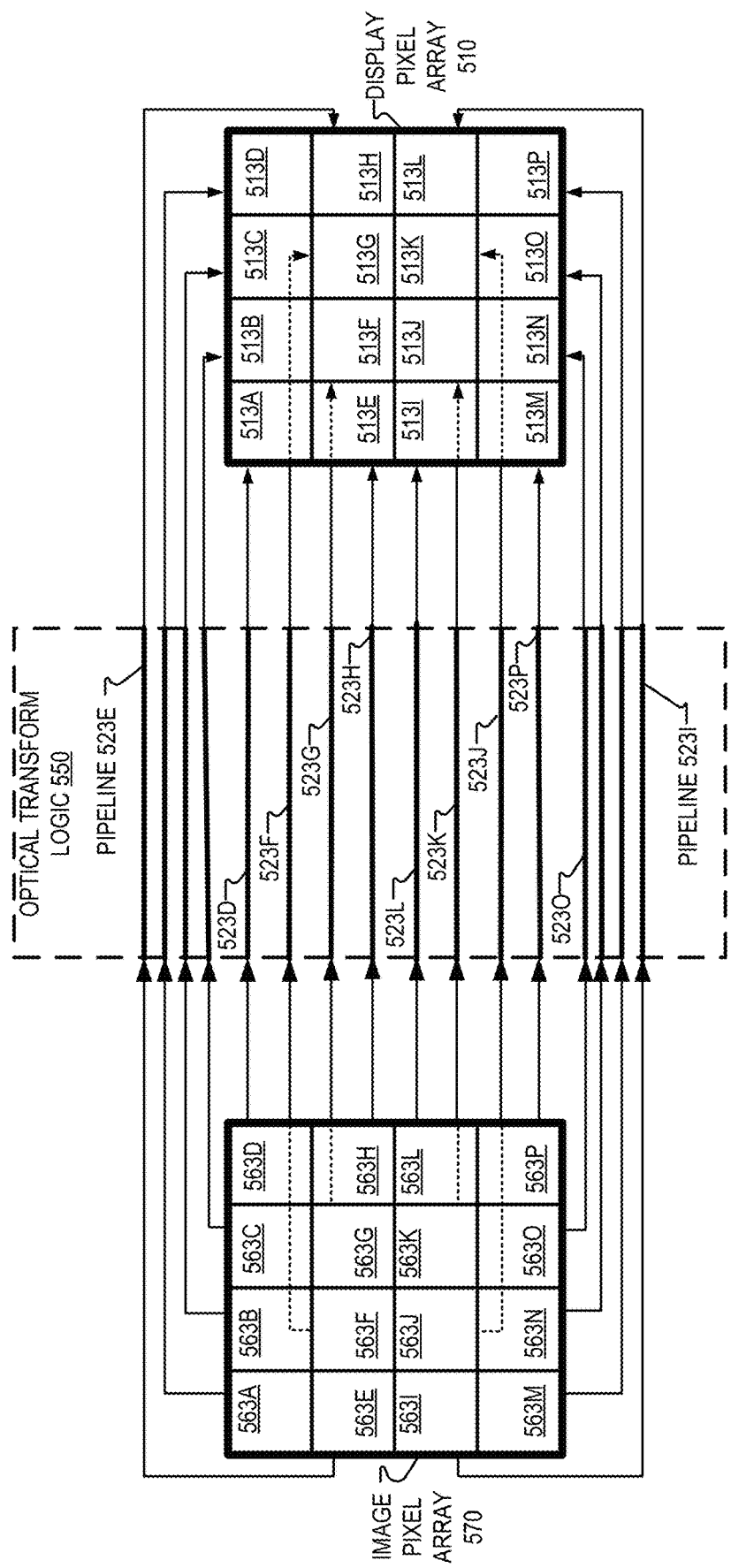
FIG. 5 illustrates example optical transform logic with dedicated parallel processing pipelines coupled between a tiled image pixel array and a tiled display pixel array, in accordance with an embodiment of the disclosure.

FIG. 5 illustrates example optical transform logic 550 with dedicated processing pipelines 523 coupled between a tiled image pixel array 570 and a tiled display pixel array 510, in accordance with an embodiment of the disclosure. Image pixel array 570 includes a plurality of image pixel tiles 563. In the illustrated embodiment of FIG. 5, there are sixteen image pixel tiles 563A-563P. Display pixel array 510 includes sixteen display tiles 513A-513P. Optical transformation logic 550 includes dedicated parallel processing pipelines 523. Each of the dedicated processing pipelines 523 is coupled between an image pixel tile 563 and a display tile 513. In the illustrated embodiment, the dedicated processing pipelines have a one-to-one correspondence between the image pixel tile and the display pixel tile. Each dedicated processing pipeline 523 is coupled to receive tiled pixel data generated by one of the image pixel tiles 563. Image pixel array 570, display pixel array 510, and optical transform logic 550 may be used as image pixel array 170/270, display pixel array 113/213, and optical transform logic 150/250, respectively. Through extensive testing, Applicants have discovered that processing tiled portions of the image pixel array to generate tiled holograms to be driven onto display tiles significantly reduces the processing time and thus increases the time efficiency of optical transform logic.

Each image pixel tile 563 may have integer x columns and integer y rows and the integer x and the integer y are both powers of two. Therefore, a tiled portion of the infrared image captured by image pixel array 570 may include pixel data including integer x columns and integer y rows and the integer x and the integer y are both powers of two. The integer x and the integer y may be a same integer. By having the pixel data be in powers of two (e.g. 256 by 256), the processing of the pixel data is optimized for digital processing.

Figure 6:
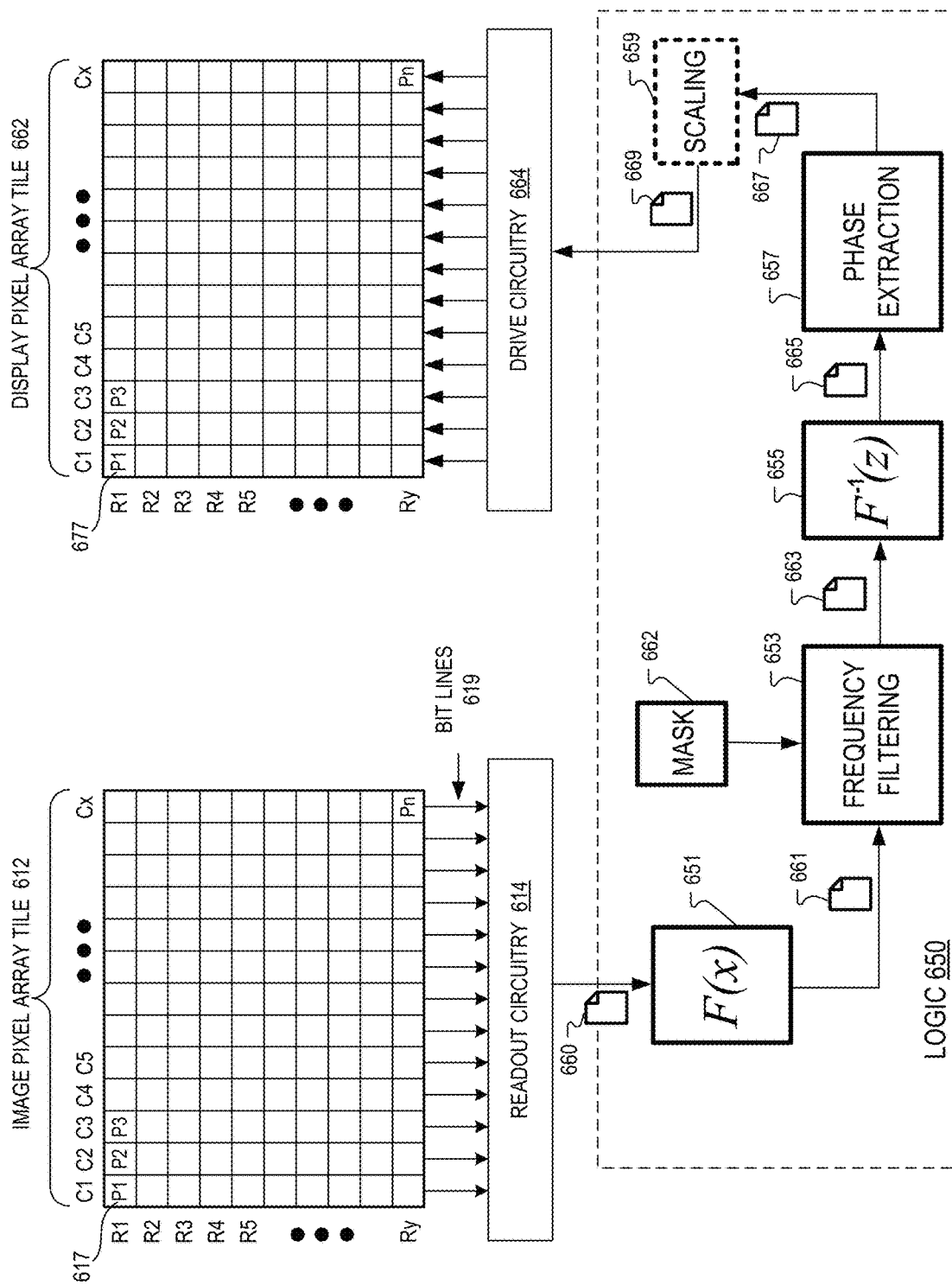
FIG. 6 illustrates example optical transform logic coupled between an image pixel array and a display pixel array, in accordance with an embodiment of the disclosure.

FIG. 6 illustrates example optical transform logic 650 coupled between an image pixel array and a display pixel array, in accordance with an embodiment of the disclosure. Each of the dedicated processing pipelines 523 in FIG. 5 may utilize optical transform logic 650. Optical transform logic 650 may be used to generate a holographic pattern for an entire display pixel array or optical transform logic 650 may be utilized to generate a tiled hologram from an image pixel tile where the tiled hologram is to be driven onto a display tile that is a portion of a display pixel array. FIG. 6 illustrates the optical transform logic 650 being included in a dedicated processing pipeline (e.g. dedicated processing pipeline 523) for a tiled architecture, but those skilled in the art will recognize that optical transform logic 650 may also be used in non-tiled architectures. Optical transform logic 650 may be included in an ASIC (Application Specific Integrated-Circuit) that includes each of dedicated processing pipelines 523. In one embodiment, a multicore processor is configured to allow each core of the processor to be a dedicated processing pipeline 523.

FIG. 6 includes an image pixel array tile 612 having image pixels 617 arranged in integer number y rows and integer number x columns. Readout circuitry 614 is coupled to read the signal value from each image pixels 617 via bitlines 619. Fourier transform engine 651 in logic 650 is coupled to receive the tiled infrared image 660 from readout circuitry 614, in FIG. 6. Fourier transform engine generates a frequency domain infrared image 661 by performing a Fourier transform on the tiled infrared image 660 received from readout circuitry 614.

Frequency filtering engine 653 is coupled to receive the frequency domain infrared image 661 from Fourier transform engine 651 and also coupled to receive mask 662. Frequency filtering engine 653 is configured to multiply the frequency domain infrared image 661 with the mask 662 to generate a filtered frequency domain infrared image 663. Mask 662 is designed to isolate the frequency of the shifted signal 143/243 for further processing. Mask 662 may include a matrix that includes '1' values for the portion of the frequency domain infrared image 661 that corresponds to the lambda-two wavelength of shifted signal 143/243 and '0' values for other portions of the frequency domain infrared image 661. In one embodiment, mask 662 is a two-dimensional Gaussian filter.

Inverse Fourier transform engine 655 is coupled to receive the filtered frequency domain infrared image 663 from frequency filtering engine 653 and configured to generate a spatial domain infrared image 665 by performing an inverse Fourier transform on the filtered frequency domain infrared image 663.

Phase extraction engine 657 is coupled to receive the spatial domain infrared image 665 and configured to extract phase data 667 from the spatial domain infrared image 665. In one embodiment, a function similar to the angle function in MATLAB software (published by Mathworks® of Natick, Mass.) is utilized to extract phase data 667. A phase value between −π and π may be generated to represent the phase data. That value may be rescaled to a value between 0 and 2π to make the value a positive value.

A scaling block 659 may also be included in logic 650 to receive the phase data 667 and scale the phase data by a scaling factor to generate scaled phase data 669. The scaling factor may represent a sizing difference between display pixels of the display tiles and image sensor pixels of the image pixel tiles.

The phase data 667 (or optionally the scaled phase data 669) is then provided to drive circuitry 664 as a holographic pattern that can be illuminated to generate the reconstructed signal 144/244.

In one embodiment, logic 650 includes a lens compensation engine (not illustrated). The lens compensation engine may be configured to multiply the phase data 667 with a lens compensation matrix that represents the lensing of optics of the system (e.g. 100/200) that logic 250 is included in. For example, viewing FIGS. 2B and 2C, the lens compensation matrix for system 200 may represent the optical properties of display pixel array 213 add to the optical properties of optical structure 280 since signal 243 passes through input optic 247, display pixel array 213, and optical structure 280 before becoming incident on image pixel array 270 while signal 244 only encounters input optic 247 as signal 244 exits system 200.

Figure 7:
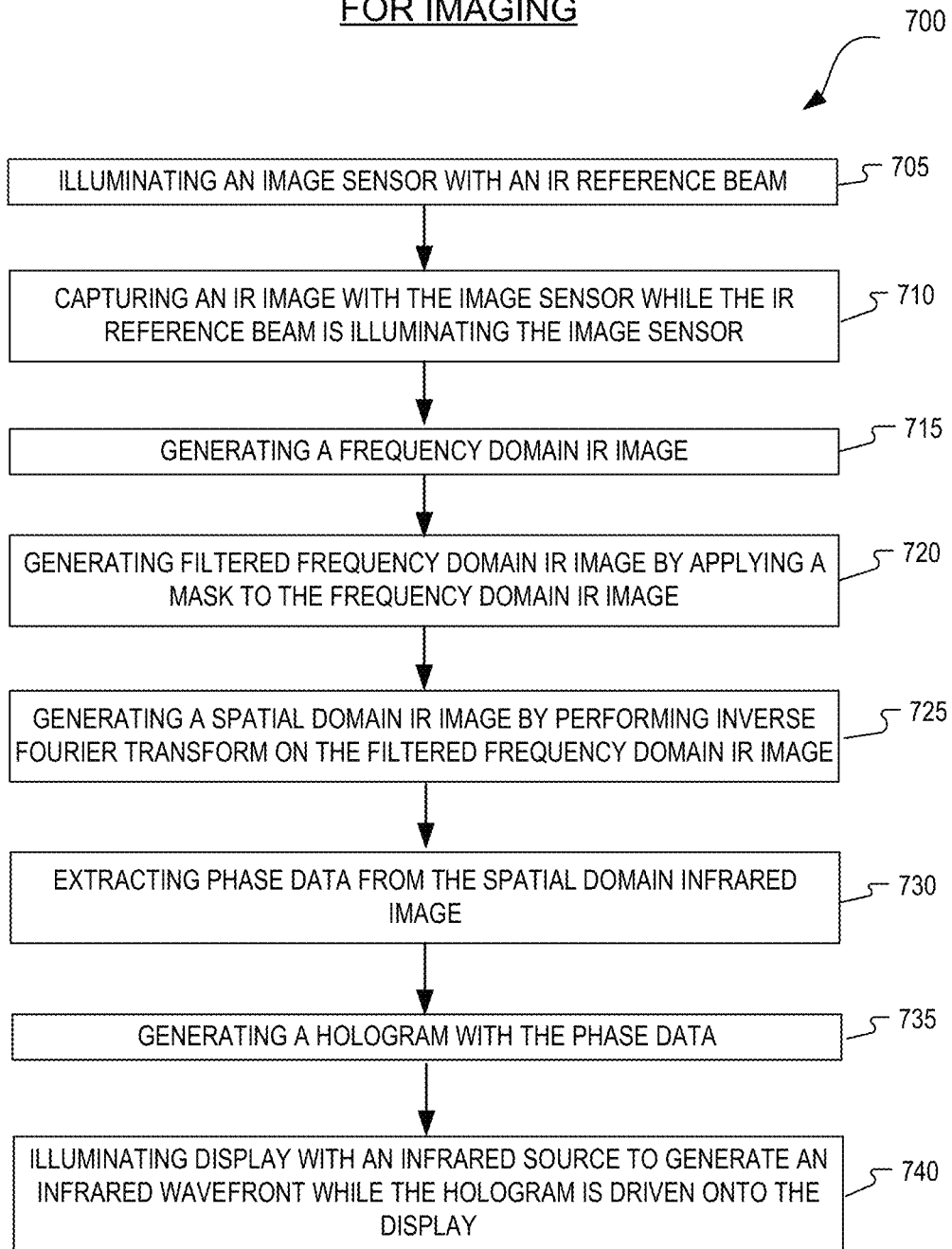
FIG. 7 illustrates a flow chart illustrating an example process of executing an optical transformation, in accordance with an embodiment of the disclosure.

FIG. 7 illustrates a flow chart illustrating an example process 700 of executing an optical transformation, in accordance with an embodiment of the disclosure. The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel. The process blocks of process 700 may be executed by system 100, system 200, or devices using components from system 100 or 200.

In process block 705, an image sensor is illuminated with an infrared reference beam (e.g. 157/257). The infrared image may include pixel data including integer x columns and integer y rows. The integer x and the integer y may both be powers of two. Both the integer x and the integer y may be the same integer.

In process block 710, an infrared image is captured with the image sensor while the infrared reference beam is illuminating the image sensor and the infrared image captures an interference between the infrared reference beam and an incoming infrared image signal (e.g. 143/243).

In process block 715, a frequency domain infrared image (e.g. 661) is generated by performing a Fourier transform operation on the infrared image. Fourier transform engine 651 may perform process block 715.

In process block 720, a filtered frequency domain infrared image (e.g. 663) is generated by applying a mask (e.g. 662) to the frequency domain infrared image to isolate a frequency representing the interference between the infrared reference beam and the incoming infrared image signal. In one embodiment, applying the mask includes multiplying the frequency domain infrared image with a matrix including values of ones and zeros. The matrix may have integer x columns and the integer y rows that are the same integer x and y from process block 705. In one embodiment, the mask is a two-dimensional Gaussian filter. Frequency filtering engine 653 may perform process block 720.

In process block 725, a spatial domain infrared image (e.g. 665) is generated by performing an inverse Fourier transform on the filtered frequency domain infrared image. Inverse Fourier transform engine 655 may perform process block 725.

In process block 730, phase data is extracted from the spatial domain infrared image. In one embodiment, extracting the phase data includes isolating an imaging number of a function representing the spatial domain infrared image. Phase extraction engine 657 may perform process block 730.

In process block 735, a hologram is generated with the phase data.

In process block 740, a display (e.g. SLM 110/210) is illuminated with an infrared source to generate an infrared wavefront (e.g. 107/207). The infrared source (e.g. 205) has a same wavelength as the infrared reference beam. The hologram generated in process block 735 is driven onto the display while the display is illuminated to generate a reconstruction (e.g. 144/244) of the incoming infrared image signal.

In one embodiment, process 700 further includes apply a lensing adjustment to the phase data. The lensing adjustment may account for a lensing of components of a device encountered by the reconstruction of the incoming infrared image signal subsequent to exiting the display. In one embodiment of process 700, the infrared reference beam is angled with respect a pixel plan of the image sensor. In one embodiment, process 700 further includes scaling the hologram by a scaling factor representing a sizing difference between display pixels of the display and image sensor pixels of the image sensor. In one embodiment, process 700 further includes scaling the hologram by a scaling factor representing a resolution difference between display pixels of the display and image sensor pixels of the image sensor.

Figure 8A:
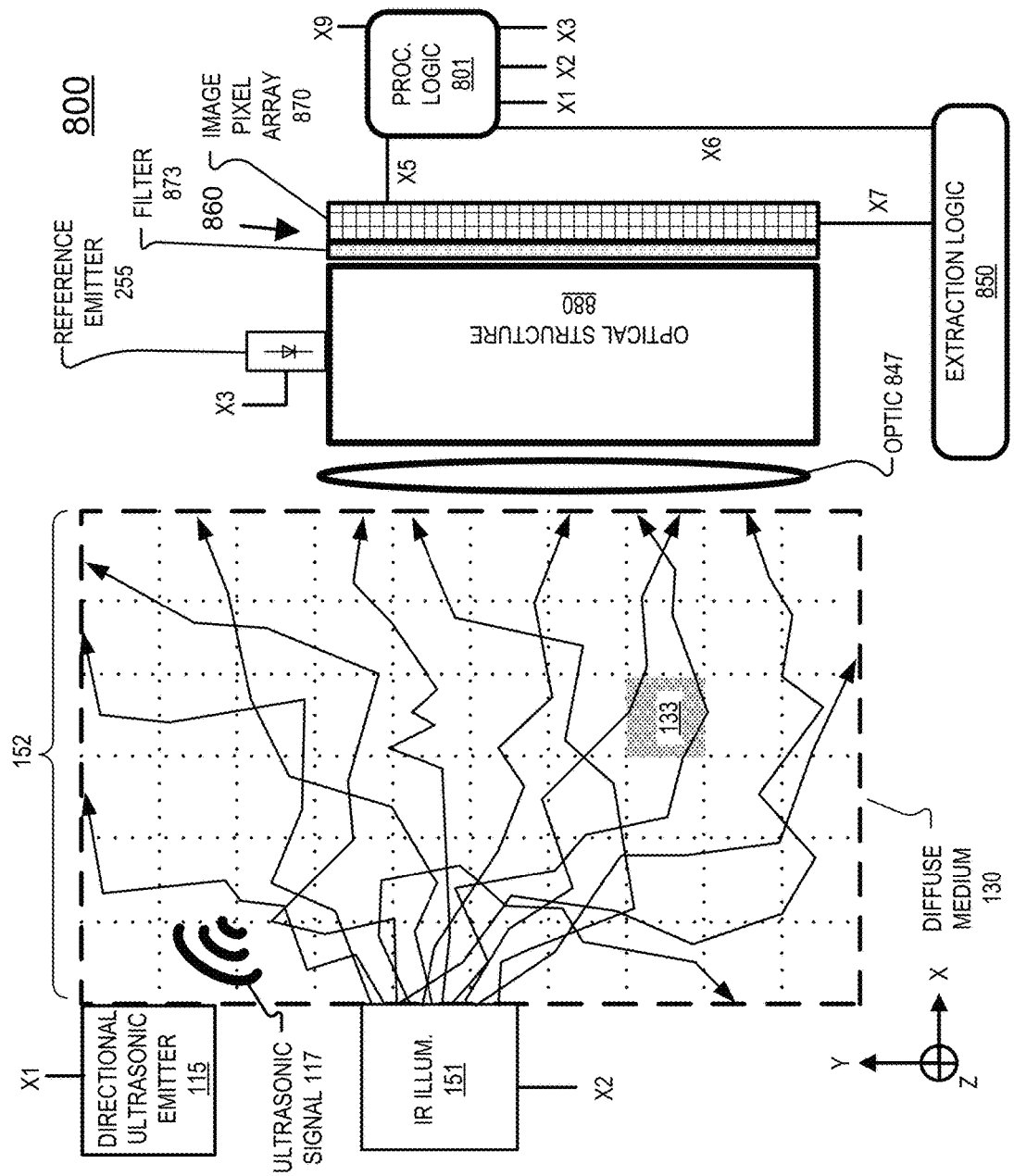
FIGS. 8A-8B illustrate an example imaging system that includes an image pixel array and extraction logic, in accordance with an embodiment of the disclosure.
Figure 8B:
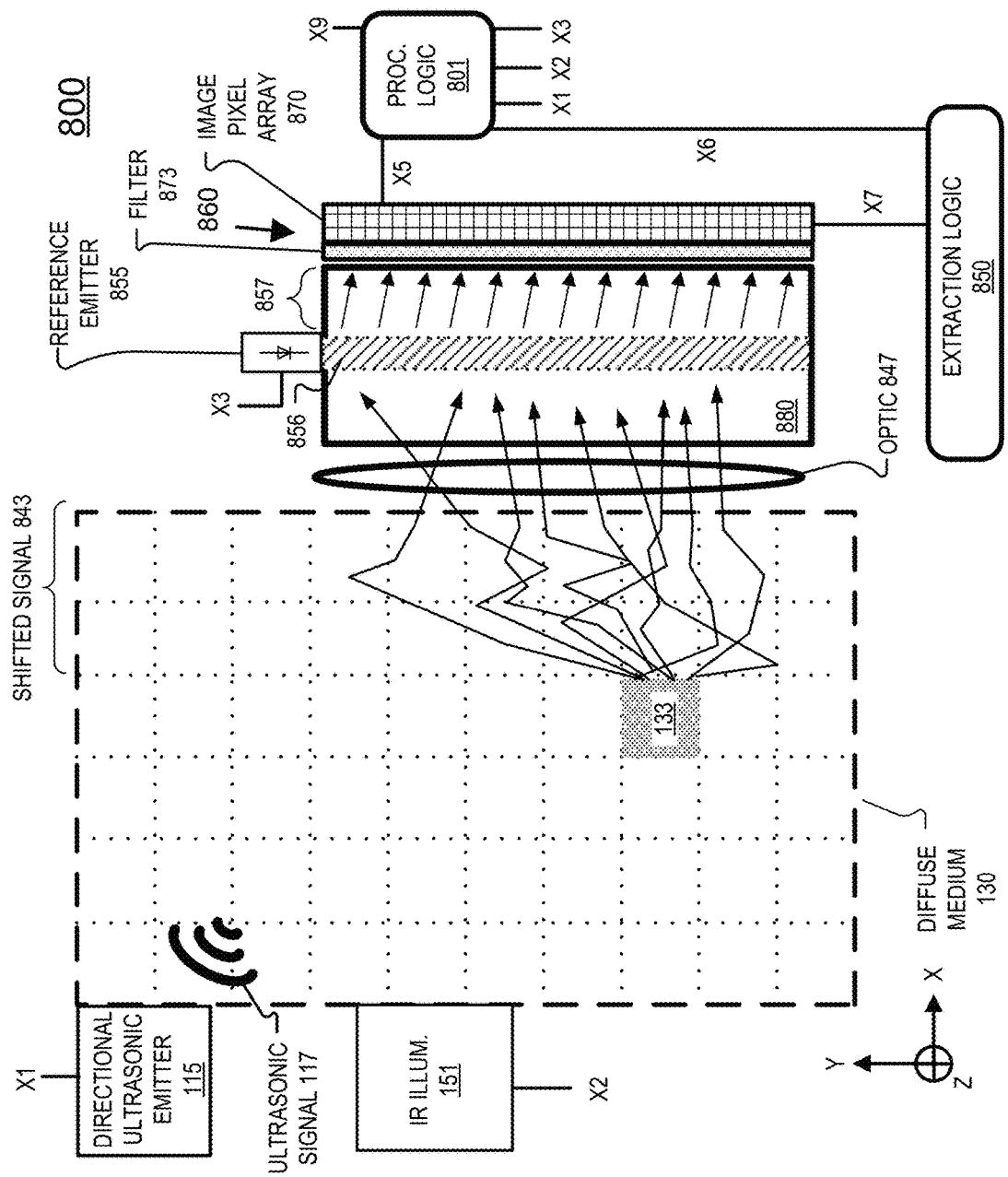

FIGS. 8A-8B illustrate an example imaging system that includes an image pixel array and extraction logic, in accordance with an embodiment of the disclosure. System 800 illustrated in FIGS. 8A-8B does not include a display pixel array, as in FIGS. 1A-2C. In FIG. 8A, processing logic 801 is coupled to drive directional ultrasonic emitter 115 to focus ultrasonic signal 117 to different locations in three-dimensional space, via output X1. Processing logic 801 is also coupled to selectively activate IR illuminator 151 via output X2, in the illustrated embodiment. System 800 may include a plurality of discrete devices that incorporate components of system 800, in some embodiments.

Imaging module 860 includes image pixel array 870 and filter(s) 873. In FIG. 8A, imaging system 800 also includes a directional ultrasonic emitter 115 coupled to be driven by processing logic 801.

Processing logic 801 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 801 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 8B, the wavelength-shifted portion of the general illumination emission 152 is illustrated as shifted infrared imaging signal 843. Being influenced by ultrasonic signal 117, shifted infrared imaging signal 843 has a different wavelength (lambda-two) than general illumination emission 152 (lambda-one).

System 800 receives (at least a portion of) shifted signal 843. An input optic 847 may optionally be included in system 800. Input optic 847 may receive shifted signal 843 and focus the shifted signal 843 to be incident on image pixel array 870. In one embodiment, input optic 847 is configured to filter out an angled portion of the shifted signal 843, as described with regard to an embodiment of input optic 147.

Still referring to FIG. 8B, reference emitter 855 is configured to selectively emit an infrared reference light having the lambda-two wavelength so that infrared reference wavefront 857 interferes with the incoming shifted signal 843. Reference emitter 855 may include one or more laser diodes and reference director optic 856 in optical structure 880 may direct the lambda-two infrared reference light to image pixel array 870 as a substantially uniform infrared reference wavefront 857. Processing logic 801 is coupled to selectively activate reference emitter 855 via output X3, in the illustrated embodiment.

Shifted signal 843 may encounter input optic 847 and optical structure 880 prior to becoming incident upon image pixel array 870. The shifted signal 843 interferes with infrared reference wavefront 857 and image pixel array 870 captures an infrared image of the interference between shifted signal 843 and infrared reference wavefront 857. In one embodiment, reference director optic 856 is configured to deliver the infrared reference wavefront 857 to the image pixel array 870 at an angle to a pixel plane of the image pixel array 870. Processing logic 801 is coupled to initiate the image capture by image pixel array 870 via output X5, in the illustrated embodiment.

In the illustrated embodiment, an infrared filter 873 is disposed between optical structure 880 and image pixel array 870. Infrared filter 873 may include the same configuration as infrared filter 173. Image pixel array 870 may include the same configuration as image pixel array 170. Image pixel array 870 is communicatively coupled to extraction logic 850 to send the captured infrared image(s) to extraction logic 850 for further processing. Extraction logic 850 is coupled to image pixel array 870 via communication channel X7, in the illustrated embodiment. Extraction logic 850 is coupled to receive the captured infrared image from the image pixel array 870 and configured to intensity data for incorporating into a composite image of diffuse medium 130.

A linear polarizer is included in system 800 to polarize shifted signal 843 to have the same polarization orientation as infrared reference wavefront 857. Reference emitter 855 may generate linear polarized light which imparts a polarization orientation to infrared reference wavefront 857. The linear polarizer may be included in optic 847, filter 873, or optical structure 880.

Figure 9:
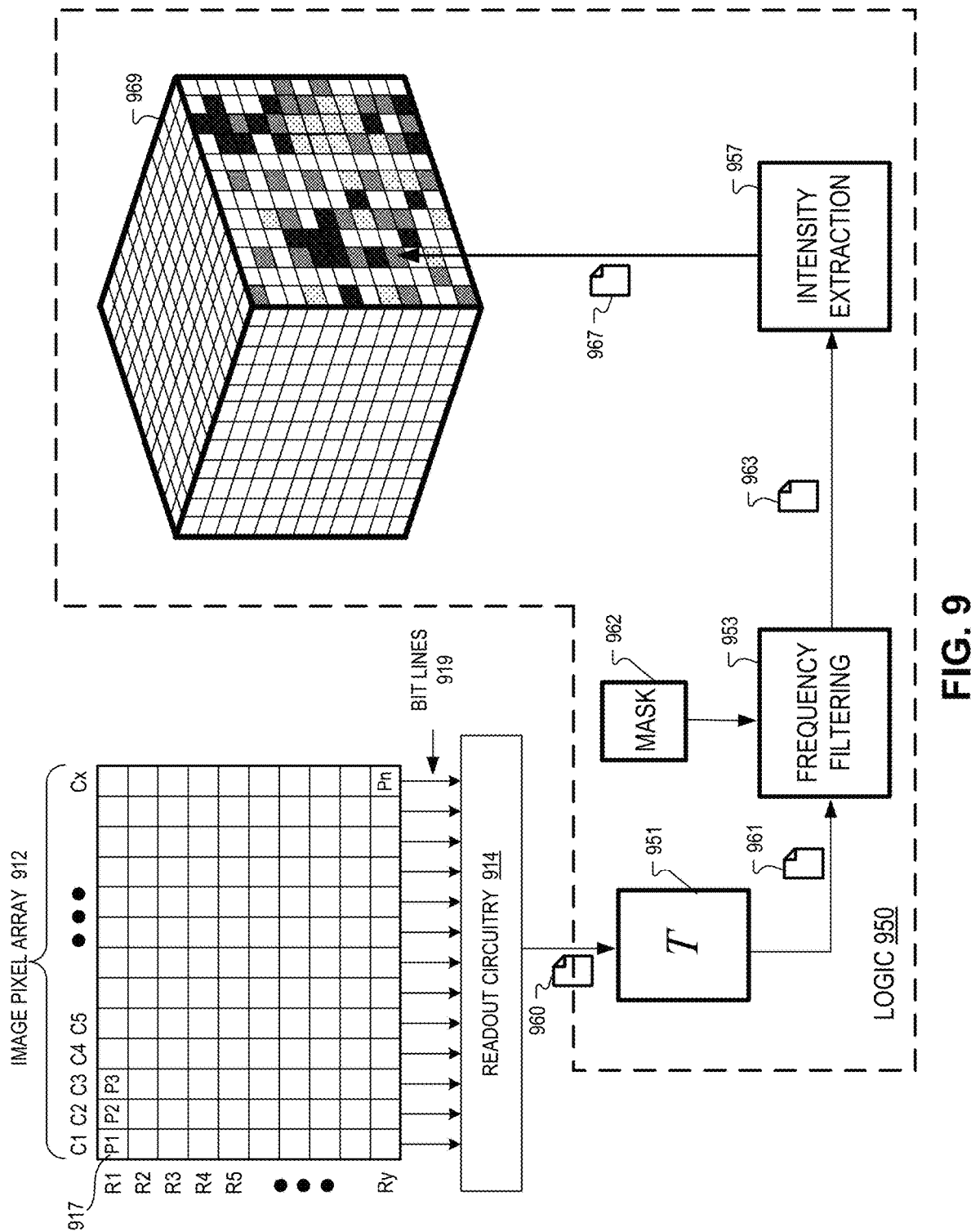
FIG. 9 illustrates an image pixel array coupled to example extraction logic, in accordance with an embodiment of the disclosure.

FIG. 9 illustrates an image pixel array 912 coupled to example extraction logic 950, in accordance with an embodiment of the disclosure. Image pixel array 912 includes image pixels 917 arranged in integer number x columns and integer number y rows. Readout circuitry 914 is coupled to read the signal value from each image pixels 917 via bitlines 919. Transform engine 951 in engine 950 is coupled to receive the tiled infrared image 960 from readout circuitry 914, in FIG. 9. Transform engine 951 generates a frequency domain infrared image 961 by performing a Transform operation on the tiled infrared image 960 received from readout circuitry 914. In one embodiment, the Transform operation includes an inverse Fourier transform. In one embodiment, the Transform operation includes a discrete cosine transform.

Frequency filtering engine 953 is coupled to receive the frequency domain infrared image 961 from Transform engine 951 and also coupled to receive mask 962. Frequency filtering engine 953 is configured to multiply the frequency domain infrared image 961 with the mask 962 to generate a filtered frequency domain infrared image 963. Mask 962 is designed to isolate the frequency of the shifted signal 843 for further processing. Mask 962 may include a matrix that includes '1' values for the portion of the frequency domain infrared image 961 that corresponds to the lambda-two wavelength of shifted signal 843 and '0' values for other portions of the frequency domain infrared image 961. In one embodiment, mask 662 is a two-dimensional Gaussian filter.

Intensity extraction engine 957 is coupled to receive the filtered frequency domain infrared image 963 and configured to extract intensity data 967 from the filtered frequency domain infrared image 963. In one embodiment, generating the intensity data 967 includes averaging intensity values of the filtered frequency domain infrared image 963. In an embodiment where a Fourier transform is used as the transform operation in Transform engine 951, the Fourier coefficients are extracted from filtered frequency domain infrared image 963 and a sum of the logarithm of the absolute value of the Fourier coefficients is calculated. The sum is then used as intensity data 967.

Intensity extraction logic 950 incorporates the intensity data as a voxel value in a composite image 969. Composite image 969 is illustrated as a three-dimensional image in FIG. 9 and may be a three-dimensional image of diffuse medium. As described in this disclosure, the system 800 may raster scan through diffuse medium 130 (focusing on different voxels) to generate a three-dimensional image of diffuse medium.

Figure 10:
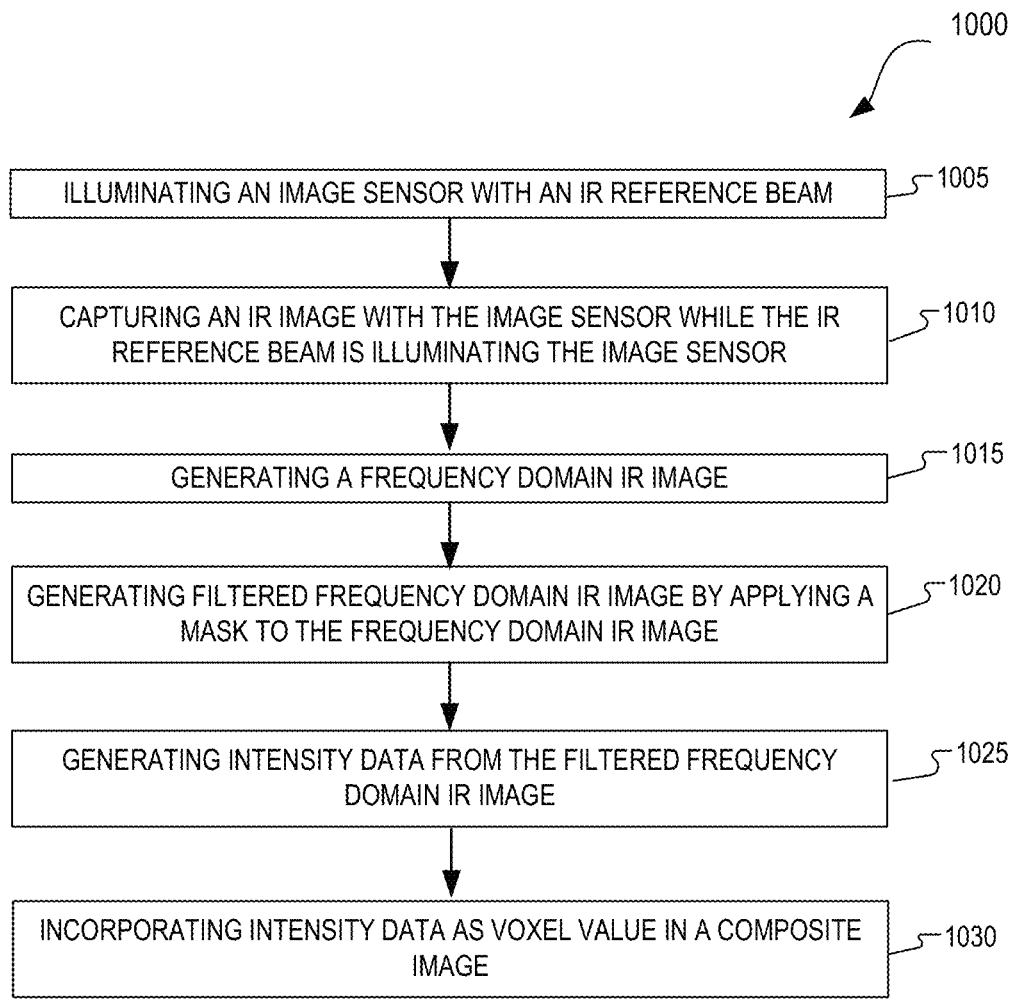
FIG. 10 illustrates a flow chart illustrating an example process of optical imaging, in accordance with an embodiment of the disclosure.

FIG. 10 illustrates a flow chart illustrating an example process 1000 of optical imaging, in accordance with an embodiment of the disclosure. The order in which some or all of the process blocks appear in process 1000 should not be deemed limiting. Rather, one of ordinary skill in the art having the benefit of the present disclosure will understand that some of the process blocks may be executed in a variety of orders not illustrated, or even in parallel. The process blocks of process 1000 may be executed by system 800 or devices using components from system 800.

In process block 1005, an image sensor (e.g. 870) is illuminated with an infrared reference beam (e.g. 857). In process block 1010, an infrared image is captured with the image sensor while the infrared reference beam is illuminating the image sensor and the infrared image captures an interference between the infrared reference beam and an incoming infrared image signal (e.g. 843).

In process block 1015, a frequency domain infrared image (e.g. 961) is generated by performing a Transform operation on the infrared image. Transform engine 951 may perform process block 1015. In one embodiment, the transformation operation includes an inverse Fourier transform. In one embodiment, the transformation operation includes a discrete cosine transform.

In process block 1020, a filtered frequency domain infrared image (e.g. 963) is generated by applying a mask (e.g. 962) to the frequency domain infrared image to isolate a frequency representing the interference between the infrared reference beam and the incoming infrared image signal. In one embodiment, applying the mask includes multiplying the frequency domain infrared image with a matrix including values of ones and zeros. In one embodiment, the mask is a two-dimensional Gaussian filter. Frequency filtering engine 953 may perform process block 1020.

In process block 1025, intensity data is generated from the filtered frequency domain infrared image. In one embodiment, generating the intensity data includes averaging intensity values of the filtered frequency domain infrared image. In an embodiment where a Fourier transform is used as the transform operation in process block 1015, the Fourier coefficients are extracted from filtered frequency domain infrared image and a sum of the logarithm of the absolute value of the Fourier coefficients is calculated. The sum is then used as intensity data.

In process block 1030, intensity data is incorporated as a voxel value in a composite image. The composite image may be a three-dimensional composite image. Logic 950 may provide the three-dimensional composite image to a network, in some embodiment.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I²C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A device comprising:
    a reference emitter configured to selectively emit infrared reference light;
    an image pixel array configured to capture an infrared image of an interference between an infrared imaging signal and an infrared reference wavefront generated by the reference emitter;
    an optical structure configured to direct the infrared reference light to the image pixel array as the infrared reference wavefront; and
    a display pixel array configured to generate an infrared holographic imaging signal according to a holographic pattern driven onto display pixels of the display pixel array, wherein the display pixel array is illuminated by an illumination wavefront having a same wavelength as the infrared reference wavefront,
    wherein the optical structure is disposed between the image pixel array and the display pixel array, and wherein the image pixel array is disposed to receive the infrared imaging signal through the display pixel array and the optical structure.

2. The device of claim 1, wherein the optical structure is configured to direct the illumination wavefront to the display pixel array.

3. The device of claim 1, wherein the optical structure includes a slim optic including a graduated gradient grating, wherein the reference emitter is disposed to emit the infrared reference light at an edge of the graduated gradient grating, wherein the graduated gradient grating is configured to increase an outcoupled percentage of the infrared reference light as a distance from the edge of the graduated gradient grating increases.

4. The device of claim 1, wherein the optical structure includes a light director including a beam splitter disposed at an angle from a pixel plane of the image pixel array, and wherein the beam splitter is disposed to receive the infrared reference light and redirect the infrared reference light to the image pixel array as the infrared reference wavefront, the image pixel array receiving the infrared imaging signal through the beam splitter.

5. The device of claim 1 further comprising:
    optical transform logic coupled to receive the infrared image from the image pixel array and provide the holographic pattern for the display pixel array, wherein the optical transform logic is configured to extract phase data of the interference captured by the infrared image, the holographic pattern generated from the phase data.

6. The device of claim 1 further comprising:
    an infrared illuminator configured to illuminate a diffuse medium with a general illumination emission, wherein the infrared imaging signal is a wavelength-shifted portion of the general illumination emission that is scattered by a voxel of the diffuse medium.

7. The device of claim 6 further comprising:
    an ultrasonic emitter configured to dynamically focus an ultrasonic signal to a given voxel of the diffuse medium; and
    processing logic coupled to the infrared illuminator and the ultrasonic emitter, wherein the processing logic is configured to focus the ultrasonic signal on the voxel and drive the infrared illuminator to illuminate the voxel with the general illumination emission while the ultrasonic signal is focused on the voxel, the processing logic also coupled to the reference emitter and the image pixel array, wherein the processing logic is configured to drive the reference emitter and initiate the infrared image capture by the image pixel array while the reference emitter and the infrared illuminator are emitting the infrared reference light and the general illumination emission, respectively.

8. The device of claim 1 further comprising:

processing logic configured to drive the display pixel array to a transmissive state while the processing logic activates the reference emitter to allow the infrared imaging signal to pass through the display pixel array to interfere with the infrared reference wavefront.

9. The device of claim 1 further comprising:

an input optic coupled to filter out an angled portion of the infrared imaging signal, wherein the angled portion of the infrared imaging signal has a plus-or-minus angle of incidence upon the input optic that is higher than an angle threshold.

10. The device of claim 9, wherein the sine of the angle threshold is approximately equivalent to a wavelength of the infrared imaging signal divided by a distance between two pixels of the image pixel array.

11. A device comprising:

reference emitter means for selectively emitting infrared reference light;

imaging means for capturing an infrared image of an interference between an infrared imaging signal and an infrared reference wavefront generated by the reference emitter means; and display means for generating an infrared holographic imaging signal according to a holographic pattern, wherein the display means is illuminated by an illumination wavefront having a same wavelength as the infrared reference wavefront, wherein the imaging means is disposed to receive the infrared imaging signal through the display means.

12. The device of claim 11 further comprising:

optical structure means for directing the illumination wavefront to the display means.

13. The device of claim 12, wherein the optical structure means is configured to direct the infrared reference light to the imaging means.

14. The device of claim 11 further comprising:

optical transform means for receiving the infrared image from the imaging means and providing the holographic pattern for the display means.

15. The device of claim 14, wherein the optical transform means is configured to extract phase data of the interference captured by the infrared image, the holographic pattern generated from the phase data.

16. The device of claim 11 further comprising:

infrared illumination means for illuminating a diffuse medium with a general illumination emission, wherein the infrared imaging signal is a wavelength-shifted portion of the general illumination emission that is scattered by a voxel of the diffuse medium.

17. The device of claim 11 further comprising:

ultrasonic emission means for dynamically focusing an ultrasonic signal to a given voxel of diffuse medium.

18. The device of claim 11 further comprising:

processing means for driving the display means to a transmissive state while the processing means activates the reference emitter means to allow the infrared imaging signal to pass through the display means to interfere with the infrared reference wavefront.

19. A device comprising:

an image pixel array configured to capture an infrared image of an interference between an infrared imaging signal and an infrared reference wavefront generated by a reference emitter; and a display pixel array configured to generate an infrared holographic imaging signal according to a holographic pattern driven onto display pixels of the display pixel array, wherein the image pixel array is disposed to receive the infrared imaging signal through the display pixel array.

* * * * *